United States Patent [19]

Kogan et al.

[11] 4,078,743
[45] Mar. 14, 1978

[54] CATALYST FOR DEHYDROGENATION OF PARAFFIN HYDROCARBONS TO OLEFINS AND METHOD OF PREPARING SAME

[76] Inventors: Samson Borisovich Kogan, Vasilievsky ostrov, 10 linia, 41, kv. 2; Natalia Robertovna Bursian, Moskovskoe shosse, 6, kv. 143; Boris Vladimirovich Pantusov, ulitsa Sedova, 82, kv. 60; Alexei Mikhailovich Moroz, prospekt Morisa Toreza, 92, kv. 15; Dmitry Sergeevich Orlov, Avtovskaya ulitsa, 34, kv. 30, all of Leningrad, U.S.S.R.

[21] Appl. No.: 699,632

[22] Filed: Jun. 24, 1976

[51] Int. Cl.² .................... B01J 21/04; B01J 23/62; B01J 27/08
[52] U.S. Cl. .................... 252/442; 252/466 PT; 260/683.3
[58] Field of Search .................... 252/442, 466 PT; 260/683.3

[56] References Cited

U.S. PATENT DOCUMENTS

| 3,793,232 | 2/1974 | Duhaut et al. ............... 252/466 PT |
| 3,892,657 | 7/1975 | Wilhelm ........................ 252/441 X |
| 3,972,806 | 8/1976 | Antos ........................... 260/683.3 |

*Primary Examiner*—W. J. Shine
*Attorney, Agent, or Firm*—Haseltine, Lake & Waters

[57] ABSTRACT

The present invention relates to catalysts for dehydrogenation of paraffin hydrocarbons to olefins in a medium of hydrogen and to a method of preparing said catalyst. The catalyst according to the present invention comprises a carrier, viz. active alumina, having deposited thereon platinum in an amount of from 0.2 to 1.0% by weight, an alkali metal in an amount of from 0.2 to 2.0% by weight and at least one of the three elements, i.e. gallium, indium and thallium in a total amount of from 0.2 to 1.0% by weight.

8 Claims, No Drawings

CATALYST FOR DEHYDROGENATION OF PARAFFIN HYDROCARBONS TO OLEFINS AND METHOD OF PREPARING SAME

The present invention relates to catalysts for dehydrogenation of paraffin hydrocarbons to olefins in a medium of hydrogen and to methods for preparing said catalysts.

Dehydrogenation products of paraffin hydrocarbons find extensive use in the chemical industry. In particular, higher linear monoolefins with a number of carbon atoms exceeding 10 are widely used in the preparation of synthetic detergents and surfactants.

Catalysts are known for dehydrogenation of paraffin hydrocarbons to olefins in a medium of hydrogen, comprising a heat-resistant carrier with a developed surface and active components deposited thereonto.

Thus, there is known a platinum catalyst supported on a carrier, such as active alumina, promoted with an alkali or alkaline earth metal. The method of preparing said catalyst resides in a double impregnation of a carrier (the latter being successively impregnated with a solution of a platinum compound and with a solution of a promoting agent), drying the impregnated carrier and calcination thereof after each impregnation. Said catalyst can also be prepared by a single impregnation of the carrier with a solution containing all the components being deposited, followed by drying the impregnation carrier and calcination thereof.

Also known in the art are platinum catalysts for dehydrogenation of paraffin hydrocarbons which catalysts contain, along with alkali or alkaline-earth metals, another promotor containing elements of Groups IV–V of the periodic system such as arsenic, germanium or lead. Methods of preparing said catalysts are similar to that described hereinabove. As a carrier for the production of these catalysts use is made mainly of active alumina with a developed surface which is prepared by conventional methods.

The prior art catalysts for dehydrogenation of paraffin hydrocarbons feature an insufficient activity which is expecially evidenced upon dehydrogenation under a low pressure approaching atmospheric pressure, i.e. under the conditions ensuring maximal yields of olefins in accordance with thermodynamic characteristics of this process. Thus, on a first of the above-described prior art catalysts employed in dehydrogenation of n-dodecane under the pressure of 1.4 atm.g, the yield of olefins does not exceed 8.6% of the starting feedstock. In a presence of an arsenic-containing catalyst, concentration of olefins in the dehydrogenation product of a mixture of $C_{11}$–$C_{14}$ n-paraffins under the pressure of 2.1 atm.g during 248 hours of dehydrogenation is 9.2–10.2% of a starting feedstock. On a catalyst promoted with an element of Group IV of the periodic system, i.e. with lead, the yield of olefins from n-tetradecane under the pressure of 1.4 atm.g is as high as 10.8%; however, test duration of the catalyst operation is only 20 hours.

It is an object of the present invention to provide a catalyst for dehydrogenation of paraffin hydrocarbons to olefins in a medium of hydrogen which, when used in the dehydrogenation process, would enable higher yields therein at a sufficiently high selectivity with respect to olefins.

It is another object of the present invention to provide a method of preparing said catalyst.

These and other objects of the present invention are accomplished by the provision of a catalyst comprising a carrier, viz. active alumina, having deposited thereonto platinum in an amount within the range of from 0.2 to 1.0% by weight, an alkali metal in an amount of from 0.2 to 2.0% by weight and at least one of the three elements, i.e. gallium, indium or thallium in a total amount of from 0.2 to 1.0% by weight.

Preferred is a catalyst containing 0.3 to 0.7% by weight of platinum, 0.5 to 1.0% by weight of lithium or potassium and 0.2 to 0.5% by weight of at least one of the three elements, i.e. gallium, indium or thallium.

Said catalyst can also contain a halogen in an amount of from 0.001 to 0.1% by weight.

The dehydrogenation catalyst according to the present invention ensures an increased yield of olefins in the process of dehydrogenation of paraffin hydrocarbons as compared to the prior art catalysts (approximately 10% higher under increased pressures and 1.5–2 times higher under atmospheric pressure); it is also characterized by a high selectivity (up to 93% at a conversion rate of 16–16.5%).

The catalyst according to the present invention can be prepared by a method comprising impregnation of a carrier, viz. active alumina, with solutions of platinum compounds, alkali metal compounds and, in accordance with the present invention, with compounds of at least one of the three elements, i.e. gallium, indium or thallium, in water or organic solvents; the impregnation is performed at a temperature within the range of from 15° to 100° C; the impregnated carrier is dried at a temperature of from 50° to 150° C and calcined at a temperature ranging from 450° to 550° C.

In the case of employing halide-containing compounds for impregnation of the carrier, it is advisable, in order to decrease the halide content in the catalyst thus improving the catalyst properties, that the dried and calcined carrier be treated with a steam-air mixture at a temperature within the range of from 450° to 550° C to a content of the halide in the catalyst within the range of from 0.01 to 0.1% by weight, followed by calcination at a temperature ranging from 450° to 550° C.

Futhermore, to achieve the same purpose, the impregnated dried and calcined carrier can be treated with an aqueous ammonia solution at a temperature of from 50° to 90° C to a content of the halide in the catalyst within the range of from 0.01 to 0.1% by weight, whereafter it should be dried at a temperature ranging from 50° to 150° C and calcined at a temperature of from 450° to 550° C.

The catalyst for dehydrogenation of paraffin hydrocarbons to olefins according to the present invention is prepared in the following manner.

A granulated carrier is impregnated with solutions of platinum compounds, alkali metal compounds and compounds of at least one of the three elements, i.e. gallium, indium or thallium. For impregnation use may be made of aqueous solutions as well as solutions in organic solvents (such as ethanol, acetone). As the starting components use may be made of soluble compounds of said elements: acids, salts, complexes, organo-metallic compounds. For the impregnation the compounds of the components being deposited are taken in such amounts which ensure deposition of platinum in an amount of from 0.2 to 1.0% by weight, alkali metal—in an amount of from 0.2 to 2.0% by weight, gallium, indium, thallium or a mixture thereof—in an amount of from 0.2 to 1.0% by weight. The components can be deposited either by separately impregnating the carrier with the corresponding solutions or by simultaneously impregnating the carrier with a solution containing all necessary components. After each impregnation the impregnated carrier is dried and then calcined.

To advantageously perform the impregnation, the impregnating solution volume should be sufficient for complete dipping of the carrier granules thereinto. After contacting under periodic stirring for 1 to 3 hours at a temperature of the solution within the range of from 15° to 25° C, the solution and carrier are heated to a temperature of from 80° to 100° C and the excessive amount of the solvent is evaporated for 1 to 2 hours under stirring.

After impregnation, the impregnated carrier, as has been mentioned hereinabove, is dried at a temperature of from 50° to 150° C, by gradually elevating the temperature for a period of from 8 to 24 hours. The impregnated and dried carrier is then calcined in a current of air gradually for a period of from 4 to 10 hours increasing the temperature from 450° to 550° C.

In the case, where during the catalyst preparation a halide is incorporated thereinto (such as chlorine in the case of impregnating the carrier with chlorine-containing compounds of platinum or promotors), the impregnated, dried and calcined carrier should be subjected to a specific treatment to reduce the halide content in the catalyst. To this end, the impregnated, dried and calcined carrier is treated with a steam-air mixture (5 to 20% by volume of water vapor) for a period of from 4 to 10 hours at a temperature ranging from 450° to 550° C to a halide content in the catalyst of from 0.01 to 0.1% by weight, followed by calcination at a temperature within the range of from 450° to 550° C. To the same effect, removal of the halide in the liquid phase upon heating may be applied such as treatment (washing-off) with an aqueous solution of ammonia at a temperature within the range of from 50° to 90° C, followed by drying at a temperature within the range of from 50° to 150° C and calcination at a temperature of from 450° to 550° C.

As a result of the reduced halide content in the dehydrogenation catalyst, its stability and selectivity are substantially increased.

The treatment intended to reduce the halide content in the catalyst may be performed either after each cycle comprising impregnation, drying and calcination, or after deposition of all the components onto the carrier.

To simplify the technology of the catalyst preparation, it is advisable to deposit all the components by a single impregnation of a carrier (on condition of compatibility of the components employed in the same solution) and to perform a single treatment to reduce the halide content in the catalyst.

For a better understanding of the present invention the following specific examples illustrating the preparation of the catalyst according to the present invention as well as examples illustrating its use in the process of dehydrogenation of paraffin hydrocarbons to olefins in a medium of hydrogen.

EXAMPLE 1

To 100 g of commercial active alumina (gamma-modification; specific surface area 190 m²/g; total pore volume 0.85 ml/g; average pore radius 130 A; bulk weight 0.65 g/ml; Na₂O content 0.02% by weight; Fe content 0.02% by weight; granule shape—cylinder with the diameter of 2 mm) an aqueous solution is added containing platinochloric acid, potassium nitrate and gallium chloride in an amount corresponding to the content of platinum, i.e. 0.75%, potassium—1.2% and gallium—0.2% by weight of the final catalyst. Total volume of the solution is 150 ml. After contacting the solution and carrier for 1 hour at a temperature of from 15° to 20° C under periodic stirring, the solution and carrier are heated and maintained for 1 hour at a temperature within the range of from 70° to 100° C to a practically complete evaporation of the excessive amount of the solvent. Wet granules are dried for 8 hours, by elevating the temperature within the range of from 50° to 130° C and further calcined in air at a temperature of 500° C for 2 hours. The calcined product is subjected to a double washing, to remove chlorine, by means of a 5% aqueous solution of ammonia at a temperature of from 50° to 70° C. The amount of the ammonia solution is employed at the rate of 2 ml/g of the catalyst. The contact time is one hour. The catalyst is further dried and calcined in accordance with the above-described procedure. Chlorine content in the final catalyst is 0.08% by weight.

The resulting catalyst is reduced in a current of dry electrolytic hydrogen at a temperature of 500° C under atmospheric pressure for 2 hours and tested in the process of dehydrogenation of n-dodecane in an on-stream plant under the following conditions:

| | |
|---|---|
| pressure | atmospheric |
| temperature | 460° C |
| space rate of the feedstock supply | 32 hr⁻¹ |
| molar ratio hydrogen:n-dodecane | 8:1 |
| test duration | 10 hours. |

The starting n-dodecane contains 1.5% by weight of isododecanes and below 0.00002% by weight of sulfur. Dienes and aromatic hydrocarbons are absent. Liquid and gaseous reaction products are analyzed by the method of gas-liquid chromatography. The test results are given in Table 1 hereinbelow.

EXAMPLE 2

A catalyst containing 0.75% by weight of platinum, 1.2% by weight of potassium and 0.5% by weight of gallium is prepared on the basis of the carrier described in the foregoing Example 1, using the impregnation technique also described in Example 1, but with the following changes:

1. The starting compounds used are gallium nitrate and potassium hydroxide.
2. Impregnation is carried out in two stages with intermediate drying at a temperature of from 50° to 150° C with gradual elevation of the temperature for 20 hours and intermediate calcination at a temperature of from 450° to 550° C for 6 hours.
3. After the first cycle of the carrier treatment (first impregnation, intermediate drying and calcination) chlorine is removed from the catalyst to a residual content thereof about 0.004% by weight. To this end, the calcined product is treated with a steam-air mixture (10 to 20% by volume of water vapor) at a temperature within the range of 450° to 550° C for 4 hours, followed by calcination at a temperature within the range of from 450° to 550° C.

During the first impregnation stage platinum is deposited onto the carrier along with gallium. The solvent used is ethanol. In the second impregnation stage potassium is deposited onto the carrier from its aqueous solution.

The thus-prepared catalyst is tested in a manner similar to that described in the foregoing Example 1. The test results are shown in Table 1 hereinbelow.

EXAMPLE 3

A catalyst containing 0.75% by weight of platinum, 0.8% by weight of lithium and 0.5% by weight of gallium is prepared according to the procedure of the foregoing Example 1, with, however, the following exceptions:
1. As the starting compound for platinum deposition use is made of a complex having the formula: $Pt(NH_3)_6(OH)_4$.
2. For a deposition of lithium and gallium use is made of nitrates.
3. Chlorine-removal stage is not conducted, since no chlorine is incorporated in the catalyst composition.

The resulting catalyst is tested in a manner similar to that described in Example 1 hereinabove. The test results are shown in Table 1 hereinbelow.

EXAMPLE 4

A catalyst containing 0.75% by weight of platinum, 0.8% by weight of lithium and 0.2% by weight of indium is prepared according to the procedure described in the foregoing Example 1, with, however, the following exceptions:
1. Lithium and indium are incorporated into the carrier in the form of nitrates.
2. Chlorine washing-off by means of ammonia solution is conducted at a temperature ranging from 70° to 90° C.
3. As the solvent for the carrier impregnation use is made of acetone mixed with water in the volumetric ratio of the components of 9:1 respectively.

The resulting catalyst is test according to the teast procedure of the foregoing Example 1. The test results are shown in Table 1 hereinbelow.

EXAMPLE 5

A catalyst containing 1.0% by weight of platinum, 2.0% by weight of cesium and 1.0 by weight of thallium is prepared according to the procedure of Example 1. As the starting compounds use is made of cesium and thallium nitrates. Washing-off by means of an aqueous ammonia solution is conducted to a residual chlorine content in the catalyst of 0.1% by weight. The thus-prepared catalyst is tested under the conditions described in the foregoing Example 1. The test results are shown in Table 1 hereinbelow.

EXAMPLE 6

A catalyst containing 0.35% by weight of platinum, 0.25% by weight of gallium and 0.8% by weight of lithium (the starting compound is lithium nitrate) is prepared in accordance with the procedure described in Example 1 hereinbefore. The carrier used is active alumina having the following characteristics:

| | |
|---|---|
| specific surface area | 170 m²/g |
| Na₂O content | 0.025% by weight |
| Fe content | 0.02% by weight |
| granule shape | spheric, with a diameter of 1.5 — 2 mm |
| crystalline modification | predominantly gamma-form. |

Washing-off with an aqueous ammonia solution is conducted to a residual chlorine content in the catalyst of 0.01% by weight.

The thus-prepared catalyst is tested by the test procedure described in the foregoing Example 1. The test results are shown in Table 1 hereinbelow.

EXAMPLE 7

A catalyst containing 0.5% by weight of platinum, 0.5% by weight of lithium, 0.5% by weight of indium and 0.5% weight of thallium is prepared according to the procedure described in the foregoing Example 1. Lithium, indium and thallium are incorporated into the catalyst in the form of the corresponding nitrates thereof.

The resulting catalyst is tested under the conditions of Example 1. The test results are shown in Table 1 hereinbelow.

EXAMPLE 8

A catalyst containing 0.2% by weight of platinum, 0.2% by weight of lithium and 0.2% by weight of indium is prepared in accordance with the procedure described in Example 1 hereinbefore. Lithium and indium are incorporated into the carrier in the form of the corresponding nitrates.

The resulting catalyst is tested by the test procedure of Example 1. The only exception resides in that after reduction with hydrogen, the catalyst is treated with a mixture of hydrogen and hydrogen sulfide (about 10 vol.% of hydrogen sulfide) at a temperature within the range of from 40° to 60° C under atmospheric pressure for one hour. The test results are shown in Table 1 hereinbelow.

EXAMPLE 9

A catalyst containing 0.35% by weight of platinum, 0.5% by weight of lithium, 0.2% by weight of gallium, 0.2% by weight of indium and 0.1% by weight of thallium is prepared in a manner similar to that described in the foregoing Example 1, with, however, the following exceptions:
1. As the starting compound for platinum deposition use is made of a complex having the formula: $Pt(NH_3)_4(NO_3)_2$.
2. For deposition of the remaining components use is made of the nitrates of lithium, gallium, indium as well as thallium tribromide.
3. The stage of treatment to reduce the halide content in the catalyst is not conducted.

The thus-prepared catalyst is tested according to the procedure described in the foregoing Example 1. The test results are presented in Table 1 hereinbelow.

The following Examples 10 to 12 illustrate the preparation and tests of the prior art dehydrogenation catalysts; the preparation and test conditions being the same as those for the catalyst of the present invention.

EXAMPLE 10

A catalyst containing 1.0% by weight of platinum and 0.5% by weight of lithium (the latter being incorporated in the nitrate form) is prepared and tested as described in Example 1 hereinbefore. The test results are shown in Table 1.

EXAMPLE 11

A catalyst containing 0.75% by weight of platinum, 0.8% by weight of lithium and 0.1% by weight of arsenic is prepared as in Example 1 hereinbefore. Therewith, lithium is incorporated in the form of lithium nitrate, while arsenic in the form of sodium arsenite.

The thus-prepared catalyst is tested in a manner similar to that described in Example 1. The test results are shown in Table 1 hereinbelow.

EXAMPLE 12

A catalyst containing 0.35% by weight of platinum, 0.5% by weight of lithium and 0.2% by weight of germanium is prepared by the procedure described in the foregoing Example 1, with, however, the following exceptions:

1. Lithium is incorporated in the nitrate form; germanium—in the form of a solution of germanium tetrachloride in 96% ethanol.
2. Chlorine removal is effected according to the procedure described in the foregoing Example 2.

The resulting catalyst is tested under the conditions of Example 1. The test results are shown in Table.

From the data presented in Table 1 it is seen that the catalyst according to the present invention (Examples 1 to 9) is substantially superior to the prior art catalysts (Examples 10 to 12) with respect to activity and selectivity under the conditions of dehydrogenation of n-dodecane thus ensuring an increased yield of olefins.

In Table 2 hereinbelow there are shown the results of lasting test runs of the catalyst according to the present invention under the conditions of dehydrogenation of mixtures of $C_{11}$–$C_{17}$ paraffin hydrocarbons under superatmospheric pressure along with appropriate test results for a conventional catalyst.

The data of Table 2 also illustrate an increased efficiency of the catalyst according to the present invention (Example 6) as compared to that of the prior art catalyst (Example 12).

Table 1

Tests of the catalysts in the process of dehydrogenation of n-dodecane under atmospheric pressure, temperature of 460° C, space velocity of the feedstock supply 32 hr$^{-1}$, molar ratio between hydrogen and n-dodecane of 8:1 and duration of the dehydrogenation of 10 hours

| | Content in the catalyst, wt. % | | | Yield, wt. % | | | |
|---|---|---|---|---|---|---|---|
| Example No. 1 | platinum 2 | alkali metal 3 | elements of III, IV or V Group of the periodic system 4 | olefins 5 | dienes 6 | aromatic hydrocarbons 7 | Selectivity, % 8 |
| 1 | 0.75 | 1.2 K | 0.2 Ga | 14.8 | 0.9 | 0.2 | 91[1] |
| 2 | 0.75 | 1.2 K | 0.5 Ga | 15.1 | 1.0 | traces | 93[1] |
| 3 | 0.75 | 0.8 Li | 0.5 Ga | 17.4 | 1.3 | 1.1 | 87[1] |
| 4 | 0.75 | 0.8 Li | 0.2 In | 16.2 | 0.7 | 1.6 | 87[1] |
| 5 | 1.0 | 2.0 Cs | 1.0 Tl | 15.8 | 0.7 | 1.0 | 89[1] |
| 6 | 0.35 | 0.8 Li | 0.25 Ga | 9.5 | 0.8 | traces | 91[2] |
| 7 | 0.5 | 0.5 Li | 0.5 In + 0.5 Tl | 17.8 | 1.0 | 1.5 | 87[1] |
| 8 | 0.2 | 0.2 Li | 0.2 In | 12.0 | 1.0 | traces | 91[2] |
| 9 | 0.35 | 0.5 Li | 0.2 Ga + 0.2 In + 0.1 Tl | 12.2 | 0.8 | 0.5 | 88[3] |
| 10 | 1.0 | 0.5 Li | — | 10.7 | 0.4 | 1.2 | 86[2] |
| 11 | 0.75 | 0.8 Li | 0.1 As | 7.0 | 0.8 | traces | 88[2] |
| 12 | 0.35 | 0.5 Li | 0.2 Ge | 10.4 | 0.9 | 1.1 | 84[2] |

Note:
[1] Total yield of the products of cracking and skeleton isomerization does not exceed 0.2% by weight.
[2] Total yield of the products of cracking and skeleton isomerization does not exceed 0.1% by weight.
[3] Total yield of the products of cracking and skeleton isomerization does not exceed 0.3% by weight.

Table 2

Tests of the catalysts in the process of dehydrogenation of paraffin fractions under increased pressure[1], molar ratio between hydrogen and paraffin hydrocarbon of 8:1 and space velocity of the feedstock supply of 32 hr$^{-1}$

| Catalyst | Paraffin feedstock | Test duration, hours | Pressure, atm. g | Temperature, °C | Olefin yield, wt. % | Hydrogen content in gas vol. % |
|---|---|---|---|---|---|---|
| from Example 6 | mixture $C_{13}$–$C_{17}$ containing 96.8% of n-paraffins | 400 | 5 | 460–470 | 10.1 | 98.5 |
| from Example 8 | mixture $C_{11}$–$C_{14}$ containing 98.5% of n-paraffins | 250 | 3 | 470–475 | 10.0 | 100 |
| from Example 12 | mixture $C_{13}$–$C_{17}$ containing 96.8% of n-paraffins | 400 | 5 | 460–470 | 9.3 | 97.5 |

Note:
[1] The tests have been performed in a plant with circulation of a hydrogen-containing gas.

What we claim is:

1. A catalyst for dehydrogenation of paraffin hydrocarbons to olefins in a medium of hydrogen consisting essentially of a carrier of active alumina, platinum in an amount of from 0.2 to 1.0% by weight, an alkali metal in an amount of from 0.2 to 2.0% by weight calculated as the metal and at least one metal selected from the group consisting of gallium, indium and thallium in a total amount of from 0.2 to 1.0% by weight calculated as the metal wherein said catalyst is prepared by impregnating said alumina with a solution of a platinum compound, an alkali metal compound and a compound of at least one metal selected from the group consisting of gallium, indium and thallium; drying the said impregnated alumina and calcining at a temperature of 450° to 550° C.

2. The catalyst as claimed in claim 1, which contains 0.3–0.7% by weight of platinum, 0.5 to 1.0% by weight of alkali metal selected from the group consisting of lithium and potassium, and 0.2 to 0.5% by weight of at least one metal selected from the group consisting of gallium, indium, and thallium.

3. A catalyst for dehydrogenation of paraffin hydrocarbons to olefins in a medium of hydrogen consisting essentially of a carrier of active alumina, platinum in an amount of from 0.2 to 1.0% by weight, an alkali metal in an amount of from 0.2 to 2.0% by weight calculated aas the metal, a halide in an amount of from 0.01 to 0.1% by weight and at least one metal selected from the group consisting of gallium and thallium in a total amount of from 0.2 to 1.0% by weight calculated as the metal wherein said catalyst is prepared by impregnating said alumina with a solution of a platinum compound, an alkali metal compound, a halide and a compound of at least one metal selected from the group consisting of gallium, indium and thallium; drying the said impregnated alumina and calcining at a temperature of 450° to 550° C.

4. The catalyst as claimed in claim 1, which contains gallium in an amount of from 0.2–1.0% by weight calculated as the metal.

5. The catalyst as claimed in claim 1, which contains indium in an amount of from 0.2–1.0% by weight calculated as the metal.

6. The catalyst as claimed in claim 1, which contains thallium in an amount of from 0.2–1.0% by weight calculated as the metal.

7. The catalyst as claimed in claim 1 consisting essentially of 0.5% platinum, 0.5% lithium, 0.5% indium and 0.5% thallium.

8. The catalyst as claimed in claim 1 consisting essentially of 0.35% platinum, 0.5% lithium, 0.2% of gallium, 0.2% of indium and 0.1% of thallium.

* * * * *